United States Patent
Razavi et al.

(10) Patent No.: US 10,058,669 B2
(45) Date of Patent: Aug. 28, 2018

(54) LOCATION DETERMINING ENDOTRACHEAL TUBE AND METHODS

(71) Applicant: Texas Heart Institute, Houston, TX (US)

(72) Inventors: Mehdi Razavi, Houston, TX (US); Christopher Levert, Houston, TX (US); Sarah Wagner, Houston, TX (US); Robin Terry, Houston, TX (US); Michael Kosh, Houston, TX (US); Joanna Nathan, Houston, TX (US)

(73) Assignee: TEXAS HEART INSTITUTE, Houston, TX (US)

( * ) Notice: Subject to any disclaimer, the term of this patent is extended or adjusted under 35 U.S.C. 154(b) by 636 days.

(21) Appl. No.: 14/405,811

(22) PCT Filed: Jun. 5, 2013

(86) PCT No.: PCT/US2013/044373
§ 371 (c)(1),
(2) Date: Dec. 5, 2014

(87) PCT Pub. No.: WO2013/184841
PCT Pub. Date: Dec. 12, 2013

(65) Prior Publication Data
US 2015/0157820 A1 Jun. 11, 2015

Related U.S. Application Data

(60) Provisional application No. 61/655,821, filed on Jun. 5, 2012.

(51) Int. Cl.
*A61M 16/04* (2006.01)
*A61B 5/00* (2006.01)
(Continued)

(52) U.S. Cl.
CPC ..... *A61M 16/0488* (2013.01); *A61B 5/04884* (2013.01); *A61B 5/063* (2013.01);
(Continued)

(58) Field of Classification Search
CPC .................................. A61M 16/04–16/0497
See application file for complete search history.

(56) References Cited

U.S. PATENT DOCUMENTS 5,069,215 A 12/1991 Jadvar et al.
5,125,406 A 6/1992 Goldstone et al.
(Continued)

FOREIGN PATENT DOCUMENTS

WO 01-32249 A1 5/2001
WO 02-053012 A2 7/2002

OTHER PUBLICATIONS

International Patent Application No. PCT/US2013/044373, International Search Report and Written Opinion dated Sep. 5, 2013, 12 pages.
(Continued)

*Primary Examiner* — Rachel T Sippel
(74) *Attorney, Agent, or Firm* — Conley Rose, P.C.

(57) ABSTRACT

A system for aiding in the proper placement of an endotracheal tube in the trachea of a patent includes an endotracheal tube having a proximal region and a distal region. At least one electrode is included on the distal region to provide an electrical stimulation signal to patient tissue. The system includes a control unit coupled to the electrode and configured to differentiate proper placement of the endotracheal tube in the patient's trachea from improper placement of the endotracheal tube in the patient's esophagus based on a sensed response to the electrical stimulation provided by the electrode.

25 Claims, 8 Drawing Sheets

(51) Int. Cl.
  *A61N 1/05* (2006.01)
  *A61M 16/00* (2006.01)
  *A61B 5/0488* (2006.01)
  *A61B 5/06* (2006.01)

(52) U.S. Cl.
  CPC ............ *A61B 5/068* (2013.01); *A61B 5/6853* (2013.01); *A61M 16/0051* (2013.01); *A61M 16/044* (2013.01); *A61M 16/0443* (2014.02); *A61M 2205/13* (2013.01); *A61M 2205/3303* (2013.01); *A61M 2230/65* (2013.01); *A61N 1/0517* (2013.01); *A61N 1/0519* (2013.01)

(56) References Cited

U.S. PATENT DOCUMENTS

| | | | |
|---|---|---|---|
| 5,785,051 | A * | 7/1998 | Lipscher ............ A61B 5/06 128/200.26 |
| 5,995,872 | A | 11/1999 | Bourgeois |
| 6,196,225 | B1 | 3/2001 | Allgeyer |
| 7,178,519 | B2 | 2/2007 | Melker et al. |
| 7,583,991 | B2 | 9/2009 | Rea |
| 7,689,275 | B2 | 3/2010 | Blomberg et al. |
| 7,774,054 | B2 | 8/2010 | Myklebust |
| 7,925,339 | B2 | 4/2011 | Wik |
| 8,019,422 | B2 | 9/2011 | Imran et al. |
| 2007/0074728 | A1 | 4/2007 | Rea |
| 2007/0156041 | A1 | 7/2007 | Rea |
| 2008/0214921 | A1 | 9/2008 | Rea |
| 2009/0118580 | A1 | 5/2009 | Sun et al. |
| 2009/0227885 | A1 | 9/2009 | Lowery et al. |
| 2010/0063376 | A1 | 3/2010 | Kartush |
| 2010/0145178 | A1 | 6/2010 | Kartush |
| 2011/0030694 | A1 | 2/2011 | Schaner et al. |
| 2011/0071379 | A1 | 3/2011 | Rea et al. |
| 2011/0191596 | A1 | 8/2011 | Brizek |
| 2011/0245647 | A1 | 10/2011 | Stanislaus et al. |
| 2011/0306861 | A1 | 12/2011 | Thramann et al. |
| 2013/0006083 | A1 | 1/2013 | Langer |

OTHER PUBLICATIONS

Dunn, Peter F. et al., "Endotracheal Tubes and Airway Appliances," Int. Anesthesiol Clin., 2000, 38, pp. 65-94.
Rudraraju, Praveen et al., "Confirmation of Endotracheal Tube Position: A Narrative Review," Journal of Intensive Care Medicine, 2009, vol. 24, No. 5, pp. 283-292.
Absolom, M. et al., "The use of impedance respirometry to confirm tracheal intubation in children," Anesthesia, 2006, 61, pp. 1145-1148.
Birmingham, Patrick K. et al., "Esophageal Intubation: A Review of Detection Techniques," Anesth. Analg., 1986, 65, pp. 886-891.
Roberts William A. et al., "The use of capnography for recognition of esophageal intubation in the neonatal intensive care unit," Pediatric Pulmonology, 1995, 19, pp. 262-268.
Foutch, Richard G. et al., "The esophageal Detector Device: A Rapid and Accurate Method for Assessing Tracheal Versus Esophageal Intubation in a Porcine Model," Annals of Emer. Med., 1992, 21:9, pp. 1073-1076.
Sullen, David J. et al., "A New Method for Positioning Endotracheal Tubes," Clinical Reports, 1975, 45(3), pp. 596-599.
Mansfield, Jeffrey P. et al., "An Acoustical Guidance and Position Monitoring System for Endotracheal Tubes," IEEE Trans. on Biomed. Engr., 1993, vol. 40, No. 12, pp. 1330-1335.
Wichakool, Warit et al., "Magnetic Endotracheal Tube Imaging Device," 30th Annual International IEEE EMBS conference, Vancouver, British Columbia, Canada, Aug. 20-24, 2008, pp. 985-988.
Cherng, Chen-Hwan et al., "Airway Length in Adults: Estimation of the Optimal Endotracheal Tube Length for Orotracheal Intubation," J. Clin. Anesth., 2002, 14, pp. 271-274.
Urso, Abbadessa S. et al., "EMG activity of pigeon oesophagus in vivo," Archives Internationales de Physiologie et de Biochimie, Jul. 1982, 90(2), pp. 83-94.
Lu, I-Chen et al., "Optimal Depth of NIM EMG Endotracheal Tube for Intraoperative Neuromonitoring of the Recurrent Laryngeal Nerve During Thyroidectomy," World J. Surg., 2008, 32, pp. 1935-1939.
Fridlund, Alan J. et al., "Guidelines for Human Electromyographic Research," Phychophysiology, 1986, vol. 23, No. 5, pp. 567-589.
Asoh, Reizo et al, "Manometry and Electromyography of the upper esophageal sphincter in the opossum," Gastroenterology, 1978, vol. 74, No. 3, pp. 514-520.
Sundaram, Krishnamurthi, "Prevention of Main-Stem Bronchus Intubation with the EMG Endotracheal Tube," Otolaryngology—Head and Neck Surgery, 2010, 142, p. 152.
Overbeek, Jos J. M. van et al., "Simultaneous manometry and electromyography in the pharyngoesophageal segment," Laryngoscope, 1985, 96, pp. 582-584.
Tokita, T. et al., "Electromyography of the esophagus and its clinical applications," Acta Otolaryngol, Oct. 1970, 70(4), pp. 269-278.
Insalaco, Giuseppe et al., "Specificity of esophageal electrode recordings of posterior cricoarytenoid muscle activity," American Physiological Society, 1989, 66 (3), pp. 1501-1505.
Sugarbaker, David J. et al., "Mechanical and electrical activity of esophageal smooth muscle during peristalsis," American Physiological Society, 1984, 246(2), pp. 145-150.

* cited by examiner

LOCATION DETERMINING ENDOTRACHEAL TUBE AND METHODS

CROSS-REFERENCE TO RELATED APPLICATIONS

This application claims priority to U.S. provisional patent application Ser. No. 61/655,821 filed Jun. 5, 2012, and entitled "Method and System for a Location Determining Endotracheal Tube," and International Patent Application Serial No. PCT/US2013/044373, filed Jun. 5, 2013, and entitled "Location Determining Endotracheal Tube and Methods," both of which are hereby incorporated by reference in their entirety.

STATEMENT REGARDING FEDERALLY SPONSORED RESEARCH OR DEVELOPMENT

Not applicable.

BACKGROUND

Intubation is a procedure used to secure an airway for patients who are not breathing adequately on their own. The most common route used in performing an intubation procedure is the orotracheal route in which an endotracheal tube ("ETT") is passed through the mouth and into the trachea in order to facilitate ventilation to the lungs and/or maintain an open airway to administer drugs.

Intubation is commonly performed by direct visualization, which requires the physician or operator to confirm the tube placement by visually verifying that the tip of the tube has passed through the glottis into the trachea. Further, many physicians use laryngoscopes (e.g., conventional, fiber optic, or video) to move the patient's tongue and epiglottis out of the way to provide a better view of the glottis. In the most basic sense, a laryngoscope is a flashlight, and thus, it only aids the physician visually.

While an intubation procedure is routine in an anesthesia setting, the procedure can present difficulties (e.g., in emergency situations where a less experienced individual is performing the procedure). Inserting the endotracheal tube in the esophagus rather than the trachea is the most common error of the intubation procedure due to the relative locations of the trachea and esophagus. In particular, the pathway to the trachea starts in the oral cavity. The back of the oral cavity is called the pharynx, which is considered the start of the throat, and the openings to the trachea and the esophagus are located at the base of the pharynx. The trachea is anterior to the esophagus. In order to properly place the tube in the trachea, physicians must angle the tube upward (i.e. toward the anterior side of the patient's body) while intubating a patient. If the physician cannot clearly see the vocal cords, which are located at the entrance to the trachea, then it is likely for the tube to end up in the esophagus because it presents an easier route for the tube to travel from the pharynx. Complications arising from a tracheal intubation procedure are most common in infants, children, and adult women (due to the relative small larynx and trachea). Additionally, patients who have a difficult airway, congenital/chronic diseases, and/or are obese are more prone to improper placement of the endotracheal tube.

BRIEF DESCRIPTION OF THE DRAWINGS

For a detailed description of exemplary embodiments of the invention, reference will now be made to the accompanying drawings in which.

DETAILED DESCRIPTION

Figure 1:
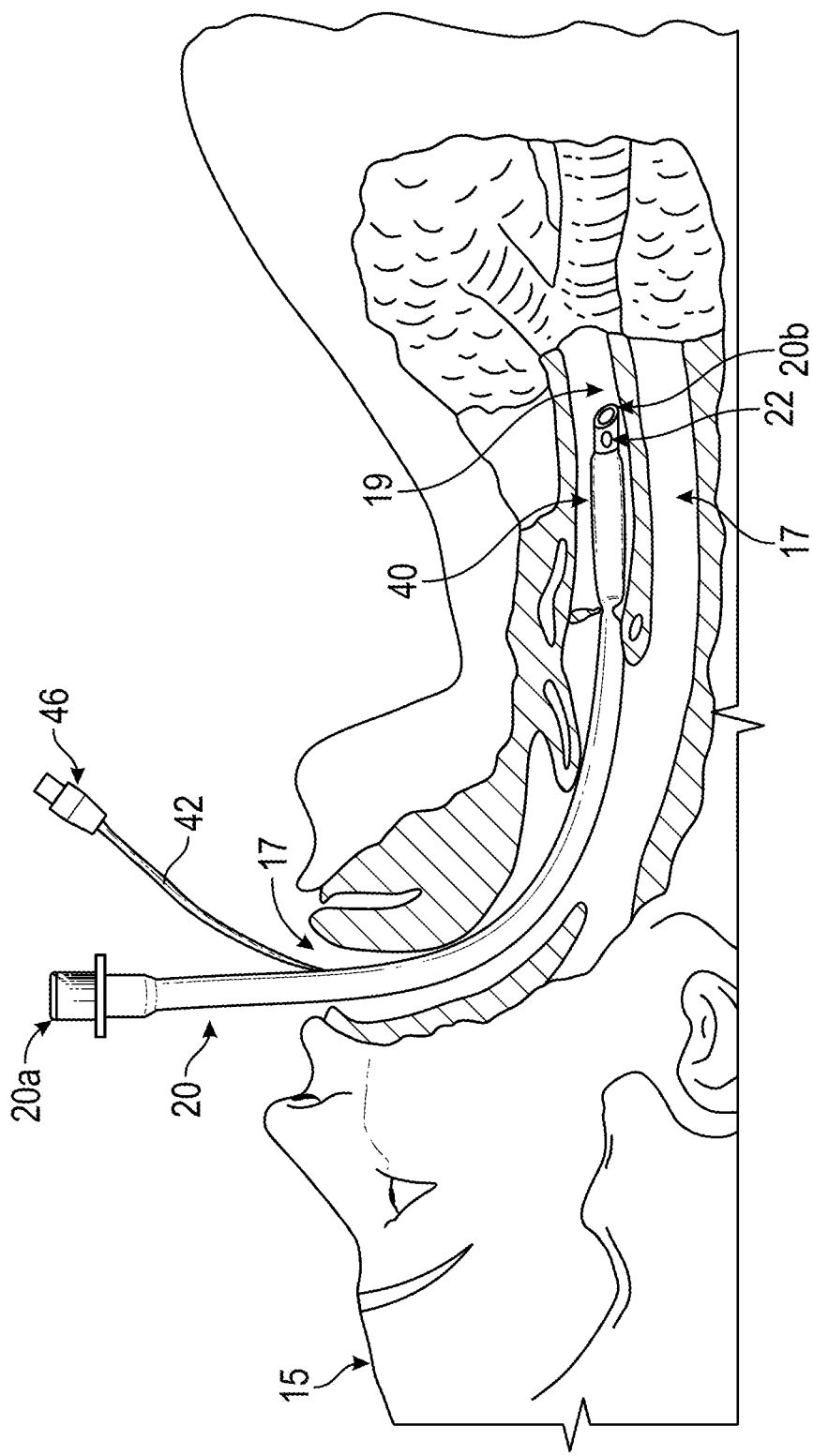
FIG. 1 is a schematic side, partial cross-sectional view of a conventional intubation process.

The following discussion is directed to various exemplary embodiments. However, one skilled in the art will understand that the examples disclosed herein have broad application, and that the discussion of any embodiment is meant only to be exemplary of that embodiment, and not intended to suggest that the scope of the disclosure, including the claims, is limited to that embodiment.

Certain terms are used throughout the following description and claims to refer to particular features or components. As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection, or through an indirect connection via other devices, components, and connections. In addition, as used herein, the terms "axial" and "axially" generally mean along or parallel to a central axis (e.g., central axis of a body or a port), while the terms "radial" and "radially" generally mean perpendicular to the central axis. For instance, an axial distance refers to a distance measured along or parallel to the central axis, and a radial distance means a distance measured perpendicular to the central axis.

As used herein, the word "approximately" means "plus or minus 10%."

Referring now to FIG. 1, wherein a typical intubation procedure is shown. During a conventional tracheal intubation procedure an endotracheal tube (ETT) 20, having a proximal end 20a and a distal end 20b, is inserted within the mount 17 of a patient 15 such that the distal end 20b is directed towards and inserted within the trachea 19 of the patient 15. Thereafter, the operator (e.g., doctor, physician, etc.) depresses a pilot balloon 46 which directs fluid (e.g., air) through a tube 42 which is in fluid communication with a distal balloon or cuff 40. Thus, when the operator depresses pilot balloon 46 fluid is directed through the tube 42 to cuff 40 which inflates to engage the inner walls of trachea 19, thus preventing fluid from flowing around tube 20. Thereafter, air is supplied through a central lumen (not specifically shown) of tube 20 from proximal end 20a toward distal end 20b which flows into the trachea 19 through one or more ventilation holes 22 disposed at the distal end 20b.

As previously described, during an intubation procedure, it is common for the operator to inadvertently insert tube 20 into the esophagus 17 of patient 15 since esophagus 17 is adjacent trachea 19 and often offers the path of least resistance for tube 20. Improper positioning of tube 20 increases the time necessary to perform the procedure and thus creates a greater of potential of causing harm to the patient 15. Thus, embodiments of a location determining endotracheal tube are disclosed herein that stimulate the tissue of a patient (e.g., patient 15) in order to provide feedback to the operator of the location of the distal end (e.g., distal end 20b) of the tube during an intubation procedure.

Figure 2:
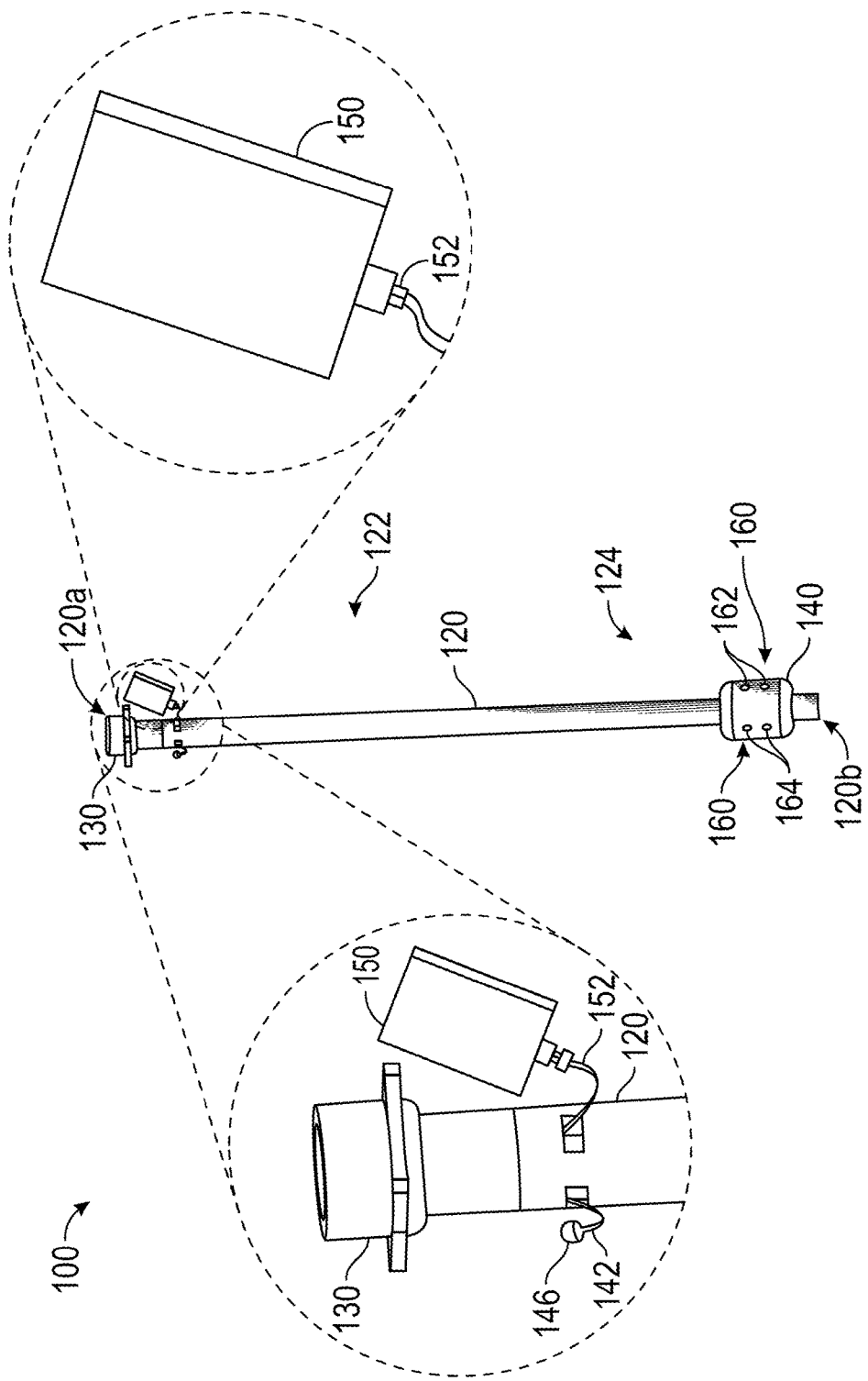
FIG. 2 is a partially schematic, perspective view of an embodiment of a location determining endotracheal tube in accordance with the principles disclosed herein.
Figure 3:
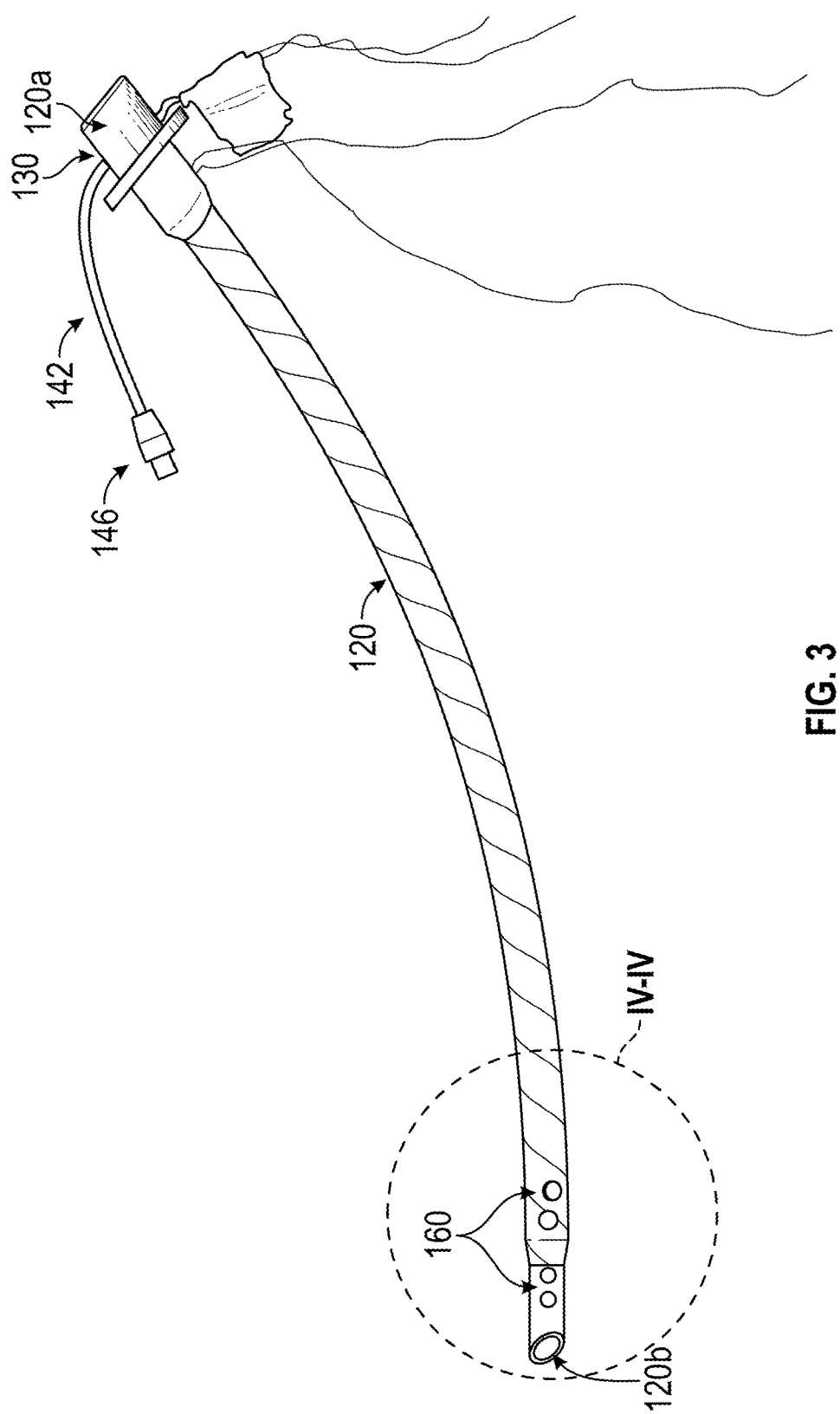
FIG. 3 is a perspective view of another embodiment of a location determining endotracheal tube in accordance with the principles disclosed herein.
Figure 4:
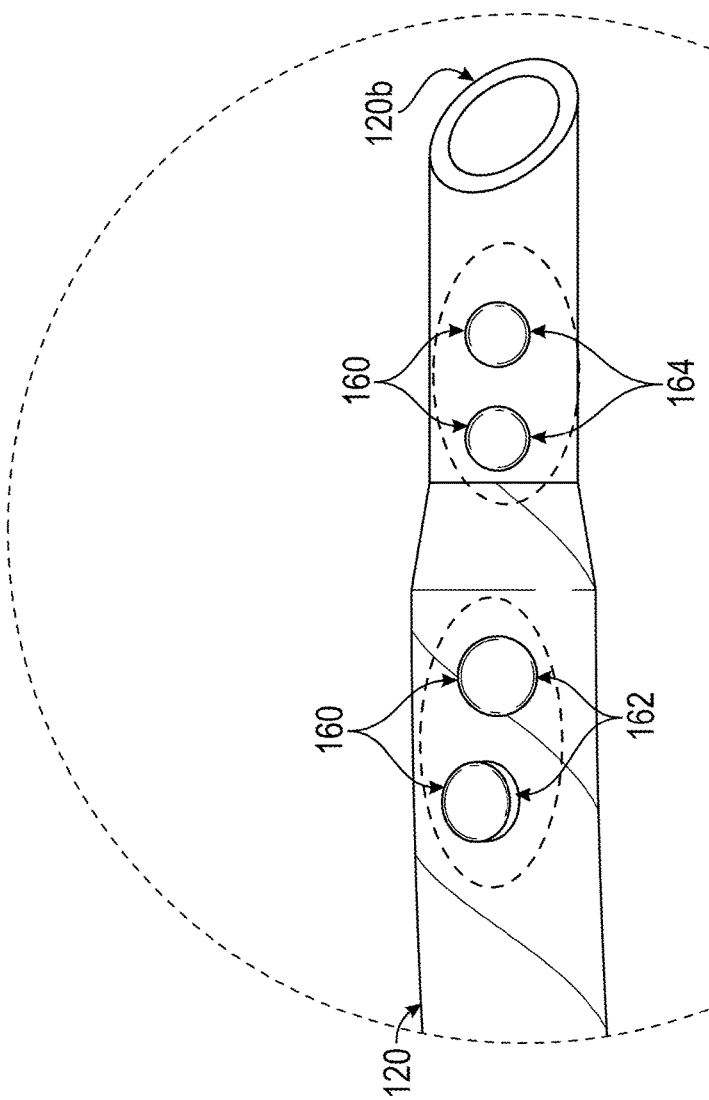
FIG. 4 is an enlarged perspective view of the location determining endotracheal tube of FIG. 3 taken along section IV-IV.

Referring now to FIGS. 2-4, wherein an embodiment of a location determining endotracheal tube 100 is shown. Tube 100 generally comprises a main tube body 120 further including a first or proximal end 120a, a second or distal end 120b opposite the proximal end 120a, a proximal region 122 extending from the proximal end 120a, and a distal region 124 extending from the distal end 120b. Tube 100 also generally includes a balloon or cuff 140 (similar to balloon 40 previously described) (note: cuff 140 is not specifically shown in FIGS. 2 and 3) disposed along the distal region 124 of body 120 between the ends 120a, 120b, and proximate the distal end 120b. Cuff 140 is coupled to a fluid communication tube 142 which is routed along tube 100 to a pilot balloon 146 (similar to balloon 46, previously described) disposed proximate proximal end 120a, thus placing balloon 146 and cuff 140 in fluid communication with one another. A standard universal adapter 130 is disposed at proximal end 120a of tube 120 and is configured to couple to a wide varied of other devices (e.g., ventilation device and/or an air supply line). In this embodiment, tube 100 also comprises a plurality of electrodes 160 disposed proximate distal end 120b. Further, in some embodiments, ventilation holes (ventilation holes 22 on tube 20) are disposed along the distal region 124 of tube 100; however, such holes are not shown in the interests of clarity.

Figure 6:
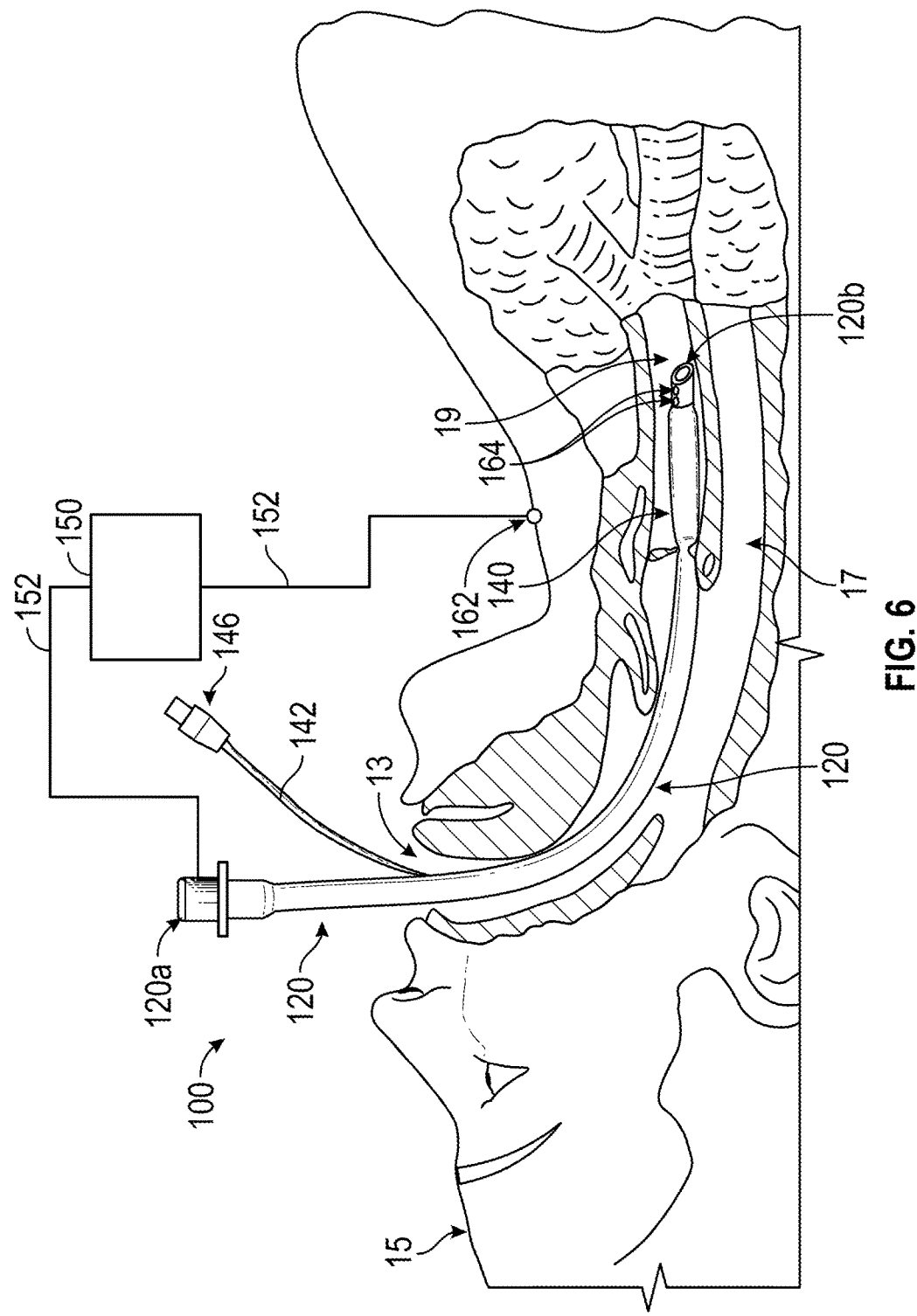
FIG. 6 is another schematic, side, partial cross-sectional view of an intubation procedure employing an embodiment of an endotracheal tube in accordance with the principles disclosed herein.

In addition, tube comprises a plurality of electrodes 160 disposed on distal region 124 of body 120 of tube 100. In the embodiment shown in FIG. 2, electrodes 160 are disposed on cuff 140, previously described; however, as will be described in more detail below, in other embodiments, the electrodes 160 may be disposed in other areas both on and proximate tube 100 while still complying with the principles disclosed herein. For example, in other embodiment electrodes 160 may be disposed near distal end 120b (such as is shown in FIGS. 3 and 4), and/or on the body of a patient (e.g., patient 15) (such as shown in FIG. 6). In some embodiments, each of the plurality of electrodes 160 is configured to emit electric current and/or sense electric current. In this embodiment, the plurality of electrodes 160 includes a pair of stimulation electrodes 162 and a pair of sensing electrodes 164. Each of the electrodes 162, 164 are electrically coupled to a control unit 150 which is disposed proximate the proximal end 120a of tube 120 (note control unit 150 is not shown in FIGS. 2 and 3). In this embodiment control unit 150 is electrically coupled to electrodes 162, 164 through a conductor 152 which is routed along tube 120; however, it should be appreciated that in other embodiments, electrodes 162, 164 may be coupled to control unit 150 through any other suitable connection such as a wireless connection (e.g., WI-FI, BLUETOOTH, Ultrasound, etc.). Additionally, in some embodiments, control unit 150 comprises a micro-processor, a power source (e.g., a battery), and/or an electrical signal generator, a user control, etc. Further, in some embodiments, the relative locations of the electrodes 162 and/or the electrodes 164 may be adjustable while still complying with the principles disclosed herein. For example, in some embodiments, electrodes 162 and/or electrodes 164 are disposed on a track that extends along body 120 of tube 100 such that a user or operator may alter or adjust the relative locations of the electrodes 162, 164 by sliding the electrodes 162 and/or electrodes 164 along the track. However, it should be appreciated that any suitable adjustment method may be utilized for the electrodes 162 and/or the electrodes 164 while still complying with the principles disclosed herein.

Figure 5:
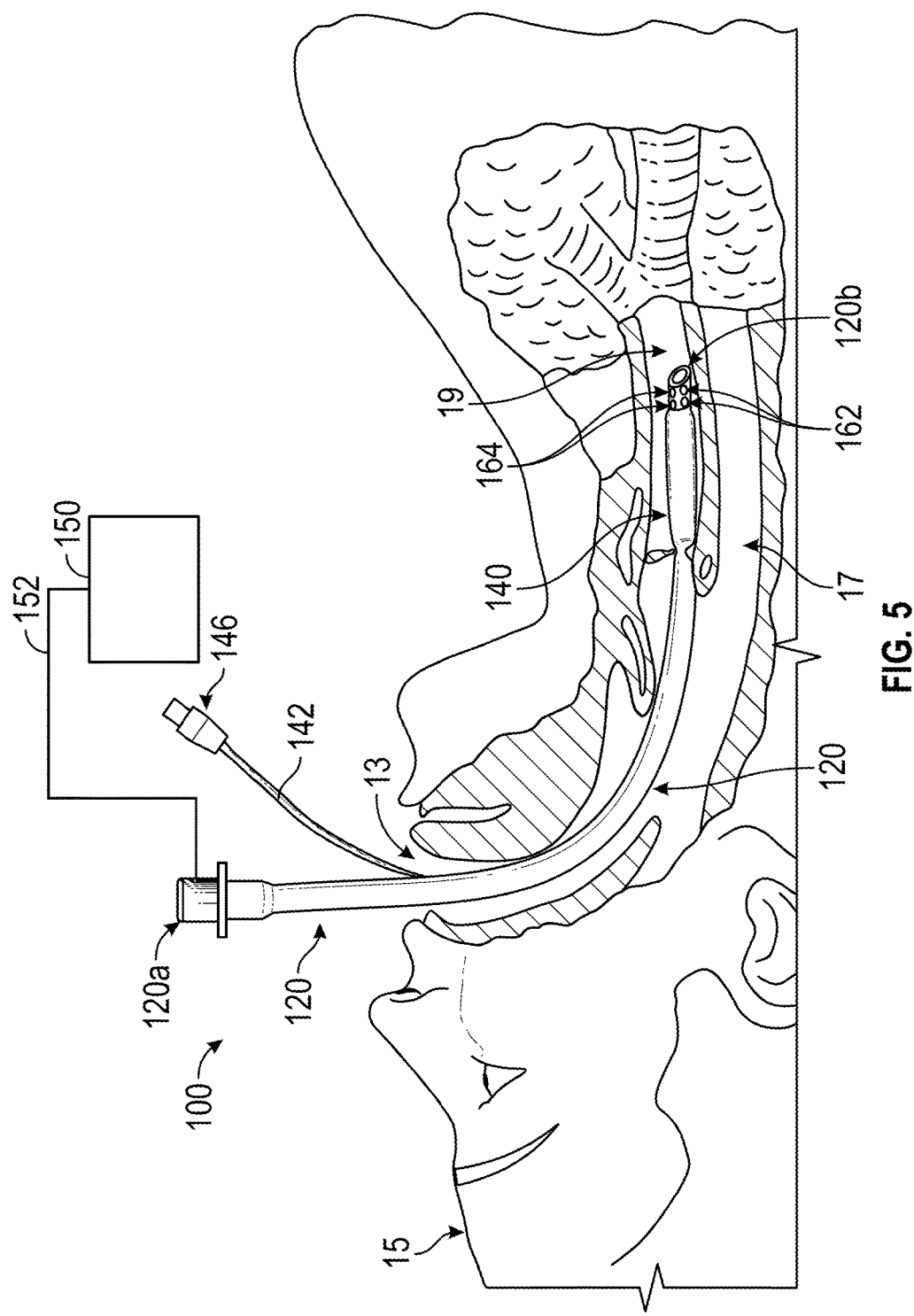
FIG. 5 is a schematic, side, partial cross-sectional view of an intubation procedure employing an embodiment of an endotracheal tube in accordance with the principles disclosed herein.
Figure 7:
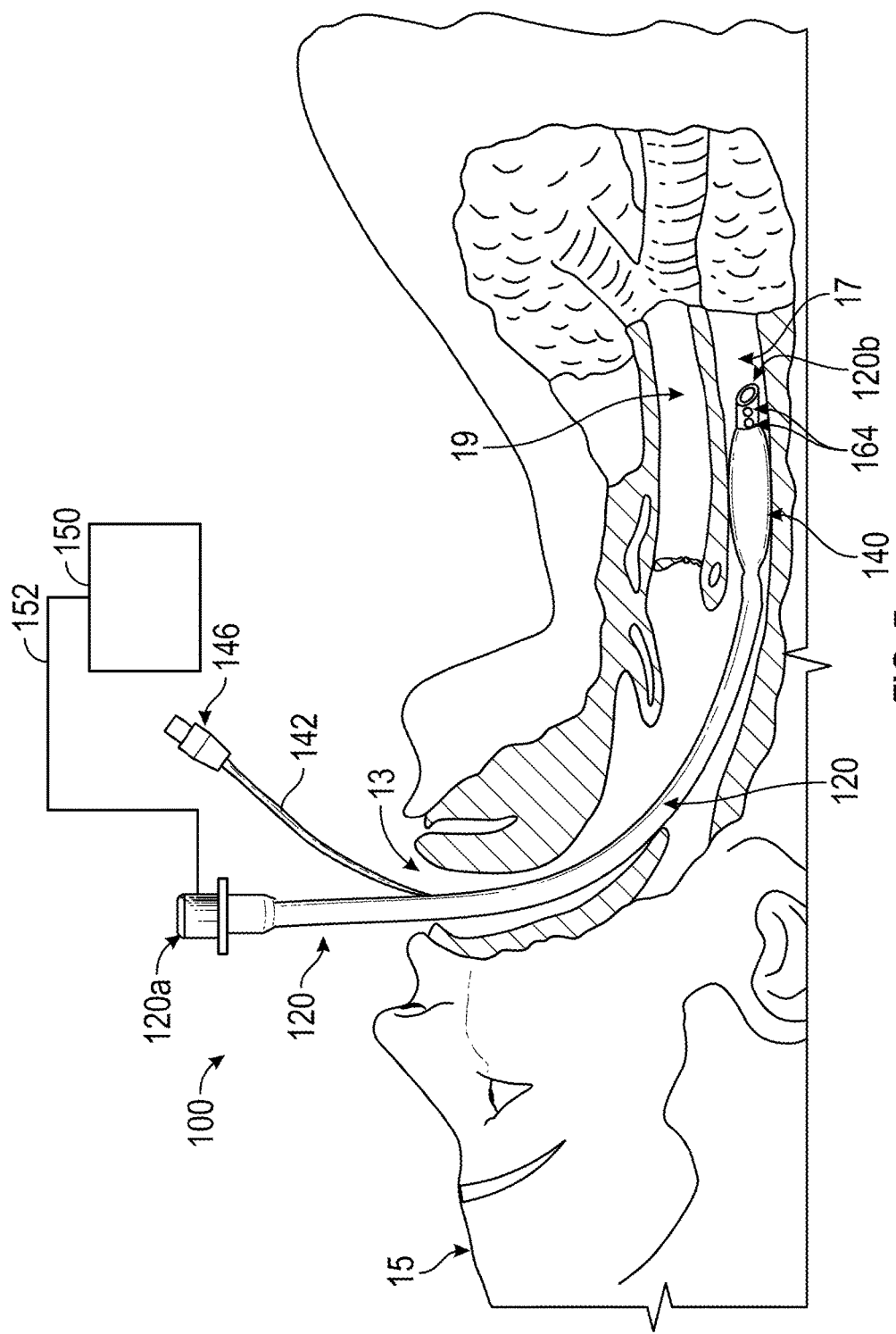
FIG. 7 is another schematic, side, partial cross-sectional view of an intubation procedure employing an embodiment of an endotracheal tube in accordance with the principles disclosed herein.

Referring now to FIGS. 5-7, the trachea 19 is composed mostly of endothelial cells and goblet cells, while the esophagus 17 is mostly smooth and skeletal muscle. Muscle tissues (such as those comprising esophagus 17) release an electrical signal that is often referred to an electromyographic ("EMG") signal when they contract. Measurable EMG signals are most often released from the esophagus 17 during peristalsis, which is the wave like contractile motion that moves food though out the digestive system. The esophagus 17 experiences three types of peristalsis: primary peristalsis, secondary peristalsis, and tertiary peristalsis. Primary peristalsis occurs on command from an electrical signal that travels to the esophagus 17 via the vagal nerve when a person swallows. Secondary peristalsis only occurs if a bolus of food becomes stuck in the esophagus 17. The mechanical stress of the trapped bolus induces multiple secondary waves that push on the bolus until it is cleared. Abnormal activity of the esophagus 17 is classified as tertiary peristalsis. When a person is unconscious (e.g., such as during a surgical procedure or emergency medical situation) the peristaltic signals are relatively infrequent, therefore naturally occurring electrical potentials cannot be reliably used in emergency situations. Thus, in some embodiments disclosed herein, electrodes (e.g., electrodes 160) are used to stimulate the muscle tissue making up the esophagus 17 and/or sense the electrical response of the muscle tissue of the esophagus 17 in order to determine whether the distal end (e.g., end 120b) of an ETT (e.g., tube 100) has been properly inserted within the trachea 19 or has been improperly disposed within the esophagus 17. In other embodiments, mechanical stimulation is utilized to stimulate the muscle tissue making up the esophagus 17 which is then sensed by electrode(s) (e.g., electrodes 164) to determine whether the distal end of an ETT has been properly inserted within the trachea 19 or is improperly disposed within the esophagus 17.

Referring specifically now to FIG. 5, in some embodiments, electrodes 162, 164 are disposed on distal region 124 of body 120 near distal end 120b. During an intubation procedure, distal end 120b of body 120 is inserted within the mouth 13 of patient 15 and is advanced toward the trachea 19 in the manner previously described above. During this procedure, an operator manipulates a user control (e.g., a button, switch, etc.) to direct control unit 150 to deliver (e.g., through a signal generator) an electric current to electrodes 162 through conductor 152 which is then transferred from electrodes 162 into the tissue of patient 15. In some embodiments, the electric current delivered from electrodes 162 comprises a series about 6 to 8 pulses each with a duration of 300-500 microseconds and separated by about 14 to 16 milliseconds. In other embodiments, the electric current delivered from electrodes 162 comprises a series of one or more pulses each having a duration of approximately 25-10,000 microseconds and separated by about 0.1 to 500 milliseconds. Thereafter, the electrodes 164 are utilized to measure or sense any electrical response which may occur after, before, and/or during the electrical stimulation by electrodes 162. If the distal end 120b of tube 120 is disposed within the trachea 19, which as is previously described above comprises mostly of endothelial cells and goblet cells, no or a relatively small electrical response is produced within patient 15. This lack of an electrical response measured or sensed by the electrodes 164 indicates to the operator that the distal end 120b of body 120 is properly placed within the trachea 19. However, if distal end 120b of body 120 is disposed within esophagus 17, the electrical pulses delivered from electrodes 162 may induce peristalsis within the esophagus 17 which in turn produces a relatively large electrical response from the muscle tissue disposed therein. Therefore, if the electrodes 164 measure or sense an elevated electrical response, such as an EMG signal, then the operator is alerted to that the distal end 120b of body 120 is improperly disposed within the esophagus 17 of patient 15. In some embodiments, the operator is alerted to improper placement of tube 100 within the esophagus 17 and/or proper placement of tube 100 within the trachea 19 of patient 15 by an indicator such as a warning light (e.g., incandescent bulb, light emitting diode ("LED"), etc.) and/or any other suitable notification device or method such as, for example, an audible alarm, a message on a display screen, a vibration signal, or some combination thereof.

Referring specifically now to FIG. 6, in some embodiments, one or more of the electrodes 162 are placed outside the body of patient 15. In particular, during an intubation procedure, one or more electrode(s) 162 is placed along the outside of the body of patient 15 and electric current is emitted therefrom in the same manner as previously described for the embodiment shown in FIG. 5 (e.g., after the operator manipulates a user control). However, in this embodiment, the electric current emitted from electrode(s) 162 is directed through the body of patient 15 and into the tissue making up trachea 19 and esophagus 17. In some embodiments, the electric current emitted from electrodes 162 travels to the tissue making up trachea 19 and esophagus 17 through a nerve such as, for example, the vagal nerve; however, it should be appreciated that the electric current may be transmitted to tissue making up trachea 19 and esophagus 17 through a wide variety of pathways within the body of patient 15 while still complying with the principles disclosed herein. As for the embodiment shown in FIG. 5, the electrodes 164 sense or measure the electrical response from the tissue surrounding distal region 124 of body 120 as a result of the electrical stimulation from electrode(s) 162. If the electrical response is small or non-existent, the operator is alerted, as previously described, that distal end 120b is properly placed within the trachea 19 of patient 15. If, on the other hand, the electrical response is elevated, such as and EMG signal which is produced during peristalsis of the esophagus 17, the operator is alerted, as previously described, that distal end 120b of tube 120 is improperly disposed within the esophagus 17 of patient.

Referring specifically now to FIG. 7, in some embodiments, an electrical response from the tissue making up either the trachea 19 or esophagus 17 is induced through mechanical stimulation in lieu of or in addition to electrical stimulation from electrode(s) 162 as previously described. For example, in these embodiments, during an intubation procedure, the operator depresses or otherwise actuates pilot balloon 146. As previously described, when pilot balloon 146 is depressed, fluid disposed therein is directed down tube 142 to cuff 140, thereby causing cuff 140 to inflate and contact the tissue surrounding distal region 124 of body 120. If, as is shown in FIG. 7, the distal end 120b of body 120 is improperly placed within esophagus 17, cuff 140 contacts the inner walls thereof and forms a block therein. The inflated cuff 140 thereafter triggers mechanical stretch receptors in the muscle tissue of the esophagus 17, which in turn initiates secondary peristalsis and causes the muscle tissue of esophagus 17 to emit an electrical response (e.g., an EMG signal) as previously described. If, on the other hand, the distal end 120b of body 120 is placed within the trachea 19, the inflated cuff 140 does not invoke a similar electrical response. As a result, during such an intubation procedure, the cuff 140 is inflated and electrode(s) 164 measure a small or no electrical response, the operator is alerted, as previously described, that distal end 120b of tube 100 is properly placed within the trachea. However, if after inflation of cuff 140, electrodes 164 measure an elevated electrical response (such as that characteristic of and EMG signal), then the operator is alerted, as previously described, that distal end 120b of body 120 is improperly disposed within the esophagus 17 of patient.

Figure 8:
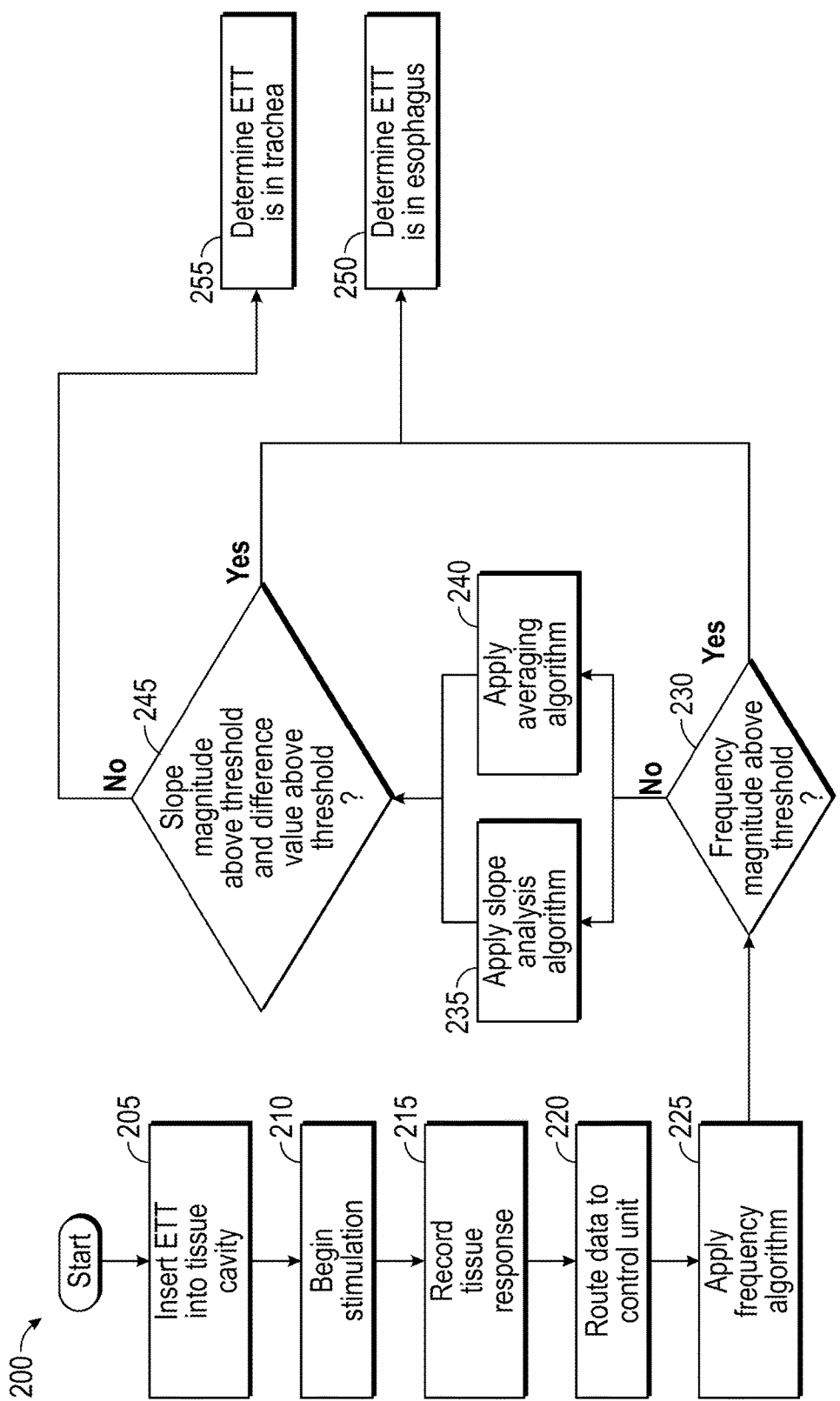
FIG. 8 is a schematic diagram of a method of performing an intubation procedure with an embodiment of an endotracheal tube in accordance with the principles disclosed herein.

Referring now to FIG. 8, wherein a logic diagram for a method 200 of operating an embodiment of a location determining endotracheal tube (e.g., tube 100) is shown. Initially, the endotracheal tube is inserted within the mouth (e.g., mouth 13) of patient (e.g., patient 15) at block 205. Thereafter stimulation, whether it be direct electrical stimulation (e.g., FIG. 5), indirect electrical stimulation (e.g., FIG. 6), and/or mechanical stimulation (e.g., FIG. 7 of the patient's tissue is initiated at block 210. The electrical response of the patient's tissue resulting from the stimulation initiated in block 210 is recorded (e.g., by electrode(s) 164, previously described) at block 215 and the data is routed to a control unit (e.g., control unit 150) at block 220. The electrical response recorded at block 215 may comprise electrical signals sensed before, during, and/or after the stimulation initiated in block 210.

In some embodiments of method 200, the raw data measured by the electrodes in block 215 goes through an initial pre-processing step once it is received by a control unit (e.g., control unit 150) at block 220. For example, in some embodiments, software within the control unit detects the starting and ending times for the stimulation applied in block 210 thus defining a "stimulation period", and then isolates any EMG response for a set time period both before and after the defined stimulation period. In particular, in some embodiments, software within the control unit sequentially scans through the raw data and marks the earliest voltage measurement that has a magnitude greater than a predetermined value as the starting time for the stimulation period. In some embodiments, the predetermined value is equal to approximately +/−0.02 V. Thereafter a set amount of time is added to this determined starting time in order to determine and ending time of the stimulation period. In some embodiments, the set amount of time that is added to the starting time is equal to approximately 0.087 seconds. Thereafter, data occurring for a period of time before the starting time (or before the stimulation period) and data occurring for a period of time after the ending time (or after the stimulation period) is retained for later analysis. For clarity, the time period occurring before the stimulation period will be referred to herein as the first period of time, and the time period occurring after the stimulation period will be referred to herein as the second time period. As will be described in more detail below, the duration of each of the first and second predetermined periods of time depends upon the specific analysis and/or algorithm to be performed.

Referring still to FIG. 8, once the data containing the electrical response from the patient's tissue is received by the control unit at block 220, software housed within control unit applies a frequency algorithm at block 225. In particular, in some embodiments, the software converts the raw data from the second time period (i.e. time occurring after the stimulation period) for a predetermined duration from a time domain to a frequency domain to produce frequency domain data. In some embodiments, the software within the control unit converts the data to the frequency domain using a Fast Fourier Transform. Once converted, the frequency domain data within a predetermined frequency range is isolated, and the maximum value of the isolated data is compared to a threshold value. In some embodiments, the duration for the second time period for the frequency algorithm may be approximately 0.35 seconds. In addition, in some embodiments, the predetermined frequency range may be approximately 6 to 10 Hz, while in other embodiments, the predetermined frequency range may be approximately 1 to 100 Hz. Further, in some embodiments, the threshold value may be approximately 15 volts.

Next, at block 230, the software within the control unit determines whether the maximum value of the frequency domain value isolated in block 225 is greater than the threshold value. If "yes", then a determination is made at block 250 that the distal end of the endotracheal tube is improperly disposed within the esophagus. If "no", then the software within the control unit is directed to perform both a slope algorithm at block 235 and an averaging algorithm at block 240.

For the slope algorithm in block 235, data is obtained from the second time period (i.e., the time period after the stimulation period) for a predetermined duration. In some embodiments, the duration of the second time period for the slope algorithm may be approximately 0.15 seconds, while in other embodiments, the duration of the second time period for the slope algorithm may range from approximately 0 to 400 milliseconds. Thereafter, the software computes a least squares linear regression fit line for the obtained data and determines the slope value for the calculated linear regression line.

For the averaging algorithm in block 240, data is obtained for both a predetermined duration from the first predetermined time period (e.g., the time period before the stimulation period) and for a predetermined duration from the second time period (e.g., the time period after the stimulation period). In some embodiments, both the first predetermined time period and the second predetermined time period for the averaging algorithm may have a duration of approximately 0.05 seconds. The software then calculates a first mean or average value of the magnitude of the voltage for the data obtained within the first time period and calculates a second mean or average value of the magnitude of the voltage for the data obtained within the second time period. The calculated second mean value is then subtracted from the first mean value to give a resulting difference value of voltage.

Referring still to FIG. 8, a determination is then made at block 245 as to whether the slope of the linear regression fit line calculated in block 235 is greater than a predetermined threshold and whether the difference value calculated in block 240 is greater than a predetermined threshold. If, in block 245, the answer to each of these inquires is "yes" (i.e., both the calculated slope and the difference value are above their respective threshold values) than a determination is made at block 250 that the distal end of the endotracheal tube is improperly disposed within the esophagus of the patient 15. If, on the other hand, the answer to either of these inquires is "no" (i.e., either the slope is not greater than the threshold value or the difference values is not greater than the threshold value) then a determination is made at block 255 that the distal end of the endotracheal tube is with the trachea of the patient. In some embodiments, the predetermined threshold value of the slope of the linear regression fit line calculated in block 235 is approximately 0.01 volts per second. In addition, in some embodiments, the predetermined threshold value of the difference value calculated in block 240 is approximately 0.00125 volts.

Thus, through use of a location determining endotracheal tube (e.g., tube 100) in accordance with the principles disclosed herein, an operator may more accurately and quickly assess with he or she has properly inserted the tube within the trachea or improperly inserted the tube within the esophagus of the patient.

While many of the embodiments described and shown herein have included a plurality of electrodes 160 on tube 100, in other embodiments, the number of electrodes 160 disposed on tube 100 may be greatly varied while still complying with the principles disclosed herein. For example, in some embodiments, only one sensing electrodes 164 may be included on tube 100; while in other embodiments, a total of two electrodes 160 are disposed on tube 100 (e.g., one electrode 162 and one electrode 164). In addition, while embodiments disclosed and shown herein have included the utilization of both an averaging algorithm and a slope algorithm, it should be appreciated that in other embodiments, either an averaging algorithm or a slope algorithm may be utilized while still complying with the principles disclosed herein. For example, in some embodiments of method 200 (shown in FIG. 8), following the analysis in block 230, only a slope algorithm is applied in block 235 and no averaging algorithm is applied in block 240. As another example, in other embodiments of method 200 (shown in FIG. 8), following the analysis in block 230, only an averaging algorithm is applied in block 240 and no slope algorithm is applied in block 235. Further, in some embodiments, tube 100 includes a switch which deactivates the electrodes 164 when the electrodes 162 are turned on and emitting electric current.

While preferred embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the invention. For example, the relative dimensions of various parts, the materials from which the various parts are made, and other parameters can be varied. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps.

What is claimed is:

1. A system for aiding in the proper placement of an endotracheal tube in the trachea of a patient, comprising:
   an endotracheal tube having a proximal region and a distal region;
   a first electrode configured to provide an electrical stimulation signal to patient tissue;
   a second electrode at the distal region of the endotracheal tube configured to sense an electromyographic response generated by patient tissue; and
   a control unit coupled to the first and second electrodes and configured to differentiate proper placement of the endotracheal tube in the patient's trachea from improper placement of the endotracheal tube in the patient's esophagus based on an electromyographic response sensed by the second electrode generated by patient tissue proximate the distal region of the endotracheal tube in response to the electrical stimulation provided by the first electrode.

2. The system of claim 1 wherein the distal region of the endotracheal tube includes, in addition to the second electrode, at least a third electrode selected from the group consisting of an electrode configured to provide electrical stimulation to patient tissue and an electrode configured to sense an electrical response from patient tissue, wherein the second and third electrodes are each coupled to the control unit.

3. The system of claim 2 wherein the first and second electrodes are each at the distal region of the endotracheal tube, and wherein the control unit is configured to provide an electrical stimulation signal to the first electrode and is configured to sense the electromyographic response on the second electrode.

4. The system of claim 1 wherein the first electrode comprises an external electrode configured to be placed outside the patient's body and to be coupled to the control unit.

5. The system of claim 4 wherein the control unit is configured to provide an electrical stimulation signal to the external electrode and is configured to sense the electromyographical response received from the second electrode.

6. The system of claim 1 wherein a location of the first electrode on the distal region is user adjustable.

7. The system of claim 1 wherein the distal region includes the first electrode, the second electrode, and at least a third electrode selected from the group consisting of an electrode configured to provide electrical stimulation to patient tissue and an electrode configured to sense an electrical response from patient tissue.

8. The system of claim 1 wherein the distal region includes a plurality of the first electrodes configured to provide an electrical stimulation signal to patient tissue and a plurality of the second electrodes configured to sense an electrical response from patient tissue.

9. The system of claim 1 wherein the control unit is configured to perform a plurality of algorithms to differentiate placement in the esophagus from placement in the trachea.

10. The system of claim 9 wherein the algorithms include at least one of a frequency algorithm, a slope algorithm and an averaging algorithm.

11. The system of claim 1 wherein the control unit includes an indicator that indicates whether the endotracheal tube is improperly in the patient's esophagus.

12. A system for aiding in the proper placement of an endotracheal tube in the trachea of a patient, comprising:
   an endotracheal tube having a proximal region and a distal region, the distal region including an electrode;
   a control unit coupled to the electrode configured to differentiate proper placement of the endotracheal tube in the patient's trachea from improper placement of the endotracheal tube in the patient's esophagus based on an electrical response sensed by an electrode contacting patient tissue proximate the distal region of the endotracheal tube;
   wherein the control unit is configured to convert the sensed electrical response from a time domain to a frequency domain to produce frequency domain data, and is configured to determine whether a maximum value of the frequency domain data over a predetermined frequency range is greater than a threshold.

13. The system of claim 12 wherein the predetermined frequency range is approximately 6 to 10 Hz.

14. The system of claim 12 wherein the control unit is configured to determine that the endotracheal tube has been improperly placed in the patient's esophagus if the maximum value of the frequency domain data over the predetermined frequency range is greater than the threshold.

15. The system of claim 14 wherein, if the maximum value of the frequency domain data over the predetermined frequency range is less than the threshold, the control unit is configured to perform both a slope algorithm and an averaging algorithm and is configured to determine that the endotracheal tube has been properly placed in the patient's trachea if both the slope and averaging algorithms confirm placement in the trachea.

16. The system of claim 15 wherein the control unit is configured to perform the slope algorithm by:
   computing a least squares linear regression fit for the sensed electrical response for a predetermined time period after a stimulation signal generated by the control unit has ended, the least squares linear regression fit including a slope value;
   determining that the endotracheal tube is improperly in the patient's esophagus if the slope value is greater than a slope threshold; and
   determining that the endotracheal tube is properly in the patient's trachea if the slope value is less than the slope threshold.

17. The system of claim 16 wherein the predetermined time period is approximately 0.15 seconds.

18. The system of claim 15 wherein the control unit is configured to perform the averaging algorithm by:
   computing a first average value of the sensed electrical response for a first predetermined time period before a stimulation signal generated by the control unit;
   computing a second average value of the sensed electrical response for a second predetermined time period after a stimulation signal generated by the control unit;
   subtracting the second average value from the first average value to produce a difference value;
   determining that the endotracheal tube is improperly in the patient's esophagus if the difference value is greater than an average threshold value; and determining that the endotracheal tube is properly in the patient's trachea if the difference value is less than the average threshold value.

19. The system of claim 18 wherein the first predetermined and second time periods are approximately 0.05 seconds and the average threshold value is approximately 0.00125 volts.

20. A method for aiding in the proper placement of an endotracheal tube in the trachea of a patient, the endotracheal tube comprising a proximal region and a distal region and at least one sensing electrode on the distal region, the method comprising:
   activating a user control on a control unit;
   electrically stimulating patient tissue;
   receiving an electromyographic signal sensed by the sensing electrode on the distal region of the endotracheal tube, the electromyographic signal being responsive to stimulating the patient tissue;
   determining whether the endotracheal tube is improperly in the patient's esophagus based on the received signal.

21. The method of claim 20 wherein electrically stimulating patient tissue comprises providing an electrical stimulation signal to a stimulation electrode in contact with the patient tissue.

22. The method of claim 20 wherein electrically stimulating patient tissue comprises inflating a cuff on the endotracheal tube.

23. A method for aiding in the proper placement of an endotracheal tube in the trachea of a patient, comprising:
   activating a user control on a control unit;
   initiating a stimulation operation;
   receiving a signal from an electrode;
   determining whether the endotracheal tube is improperly in the patient's esophagus based on the received electrical signal from the electrode;
   wherein determining whether the endotracheal tube is improperly in the patient's esophagus comprises converting the received signal from a time domain to a frequency domain and determining whether a maximum value of the frequency domain data over a predetermined frequency range is greater than a threshold.

24. The method of claim 23 wherein determining whether the endotracheal tube is improperly in the patient's esophagus comprises performing both of a slope algorithm on the received signal and an averaging algorithm on the received signal, and determining that the endotracheal tube is improperly in the esophagus if both algorithms confirm the endotracheal tube is in the esophagus.

25. The method of claim 24 wherein both the slope and the averaging algorithm are used on the received signal to determine whether the endotracheal tube is improperly in the patient's esophagus.

* * * * *